United States Patent [19]

Vartuli et al.

[11] 4,292,202

[45] Sep. 29, 1981

[54] PREPARATION OF A VANADIUM(IV)BIS(METAPHOSPHATE) HYDROCARBON OXIDATION CATALYST CONTAINING A GROUP VIB METAL PROMOTER

[75] Inventors: James C. Vartuli, West Chester, Pa.; Lee R. Zehner, Dublin, Ohio

[73] Assignee: Atlantic Richfield Company, Los Angeles, Calif.

[21] Appl. No.: 105,366

[22] Filed: Dec. 19, 1979

[51] Int. Cl.³ .................... B01J 27/14; B01J 31/02; C07D 307/60

[52] U.S. Cl. .................... 252/435; 252/430; 252/437; 260/346.75

[58] Field of Search .................... 252/430, 435, 437

[56] References Cited

U.S. PATENT DOCUMENTS

| | | | |
|---|---|---|---|
| 3,031,508 | 4/1962 | Etherington et al. | 252/437 X |
| 3,238,254 | 3/1966 | Kerr | 252/437 |
| 3,366,648 | 1/1968 | Kerr | 260/346.75 |
| 3,904,652 | 9/1975 | Frank | 260/346.75 |
| 3,907,835 | 9/1975 | Kobylinski et al. | 260/346.75 |
| 3,975,300 | 8/1976 | Burress | 252/435 |
| 3,980,585 | 9/1976 | Ken et al. | 252/435 X |
| 4,116,868 | 9/1978 | Mount et al. | 252/435 X |
| 4,147,661 | 4/1979 | Higgins et al. | 252/435 |
| 4,165,299 | 8/1979 | Pedersen | 252/435 |

*Primary Examiner*—Delbert E. Gantz
*Assistant Examiner*—William G. Wright
*Attorney, Agent, or Firm*—Delbert E. McCaslin

[57] ABSTRACT

A method for the preparation of a chromium, molybdenum or tungsten (Group VIB metal) promoted single phase vanadium(IV)bis(metaphosphate) catalyst useful for the vapor phase oxidation of hydrocarbons and particularly the oxidation of linear $C_4$ unsaturated olefins to prepare maleic anhydride.

17 Claims, No Drawings

PREPARATION OF A VANADIUM(IV)BIS(METAPHOSPHATE) HYDROCARBON OXIDATION CATALYST CONTAINING A GROUP VIB METAL PROMOTER

BACKGROUND OF THE INVENTION

This invention is directed to a novel method for the preparation of a Group VIB metal promoted single phase crystalline vanadium(IV)bis(metaphosphate) catalyst which provides good yields of and selectivities to maleic anhydride by the oxidation of unsaturated aliphatic hydrocarbons.

Prior art processes are known for the preparation of phosphorus-vanadium-oxygen catalyst systems which include other metals or metal compounds as potential yield improving co-catalysts such as molybdenum, copper, and uranium oxides or other oxides incorporated into the catalyst system during preparation. These catalysts systems however, as well as other catalysts showing some activity for the production of maleic anhydride have generally proven to be unsatisfactory for commercial application and leave a lot to be desired since the yield and selectivity to maleic anhydride is usually low.

Phosphorus-vanadium-oxygen catalysts are usually prepared by reducing vanadium pentoxide to vanadium(IV) in water or an organic solvent with a suitable reducing acid or agent. A source of phosphorus, usually phosphoric acid, is mixed with the vanadium solution to produce a catalyst precursor which is heated to give the production catalyst. Co-catalysts are usually incorporated into the catalyst system during the solution stage of preparation and by such process there is a risk of also reducing the co-catalyst or added metal compound. The present invention avoids this problem.

U.S. Pat. No. 3,907,835 discloses the preparation of a catalyst comprising an admixture of vanadium, uranium, phosphorus and oxygen for the gas phase preparation of maleic anhydride.

U.S. Pat. No. 3,904,652 describes a solution or "reflux" method for the preparation of a phosphorus-vanadium-oxygen complex catalyst containing one or more activators selected from zinc, copper, bismuth or lithium intimately combined therewith.

U.S. Pat. No. 3,366,648 describes a solution method employing reducing agents to form a vanadium-phosphorus catalyst complex along with a phosphorus stabilizer of an alkali metal (Group 1a metal) compound useful for the preparation of maleic anhydride.

There is no known prior art which describes the preparation of a Group VIB metal, i.e., chromium, molybdenum or tungsten promoted crystalline VO(PO$_3$)$_2$ hydrocarbon oxidation catalyst employing a liquid phase reaction of vanadyl sulfate, a group VIB metal oxide, acetic anhydride and phosphorus pentoxide followed by a thermal treatment with the liberation of gases to form a catalyst precursor.

SUMMARY OF THE INVENTION

This invention relates to a novel method for the preparation of a single phase crystalline vanadium(IV)bis(metaphosphate) catalyst containing a Group VIB metal of the Periodic Table with improved catalytic activity for an air or oxygen partial oxidation of an unsaturated aliphatic hydrocarbon such as 1-butene, 2-butene and 1,3-butadiene or mixtures thereof at temperatures of from about 300° C. to 600° C. by contacting the hydrocarbon and air or oxygen with the Group VIB metal promoted vanadium(IV)bis(metaphosphate) catalyst at contact times of from about 0.2 to 5 seconds of reactant feed over the catalyst, prepared by the instant method.

It is a primary object of this invention to provide a novel method for the preparation of a Group VIB metal, i.e., a chromium, molybdenum or tungsten promoted single phase crystalline vanadium(IV)bis(metaphosphate) catalyst useful as an oxidation catalyst for the preparation of maleic anhydride.

It is another object of this invention to provide a novel method of adding a Group VIB metal, in the form of its oxide, to a vanadium-phosphorus-oxygen catalyst system and thus ultimately forming, apparently by some chemical interaction and not by mere physical admixture, a Group VIB metal promoted VO(PO$_3$)$_2$ oxidation catalyst having intrinsic surface areas of from about 5 to 15 m$^2$/g. or higher.

These and other objects and advantages of this invention will become apparent from the description of the invention which follows and from the claims.

DESCRIPTION OF THE INVENTION

In accordance with the present invention, a Group VIB metal (chromium, molybdenum or tungsten) promoted single phase crystalline vanadium(IV)bis(metaphosphate) VO(PO$_3$)$_2$ compound is prepared by a novel method which, in addition to providing a chromium, molybdenum or tungsten containing catalyst useful as a hydrocarbon oxidation catalyst, also improves the intrinsic surface area of such catalyst as compared to known crystalline VO(PO$_3$)$_2$ catalyst preparation methods shown for example in U.S. Pat. No. 4,165,299.

The instant method for the preparation of the novel improved Group VIB metal promoted single phase crystalline oxidation catalyst involves a liquid phase interaction between vanadyl sulfate (VOSO$_4$), an oxide of a Group VIB metal, acetic anhydride and phosphorus pentoxide forming a slurry with the liberation of exothermic heat. Excess liquid is generally decanted from the resulting slurry which is then subjected to a thermal treatment for a period sufficient for the liberation of gases and the forming of a Group VIB metal (chromium, molybdenum or tungsten)-phosphorus-vanadium reaction product. The undecanted slurry may per se be subjected to thermal treatment with the acetic anhydride being vaporized off along with the gases. Stoichiometric amounts of the vanadyl sulfate and phosphorus pentoxide are generally employed in preparing the Group VIB metal promoted VO(PO$_3$)$_2$ compound but excess amounts may also be employed and the excess residue removed, by water washing, after reaction, to form the catalyst precursor. The molar ratio of the Group VIB metal to vanadium, employed in the process in the form of vanadyl sulfate and a Group VIB metal oxide will generally be in the range of from about 1:10 to 1:150 preferably 1:90 although larger or smaller amounts may be employed. The amount of acetic anhydride employed in the process can range from about 1 to 4 moles preferably 2 to 3 moles per mole of the combined vanadyl sulfate, phosphorus pentoxide and Group VIB metal oxide present. Greater amounts of acetic anhydride may be used but generally are not required to provide the desired promoted VO(PO$_3$)$_2$ catalyst.

The liquid phase reaction is generally carried out at ambient temperatures, e.g., 20° C. to 25° C. although higher or lower temperatures may be used. The thermal treatment of the slurry mixture will proceed at temperatures of at least 325° C. and temperatures as high as 475° C. or higher may be used to liberate the reaction gases. It is generally preferred to carry out the thermal treatment at a temperature of between about 400° C. and 460° C. to obtain a convenient rate of reaction.

After preparation and water washing, the Group VIB metal promoted $VO(PO_3)_2$ compound is generally dried at 120° C. calcined in air at temperatures between about 450° C. and 500° C. or higher for at least two hours, then broken up and sieved to the appropriate Tyler Standard Sieve mesh size, usually for fixed bed reactor use. The resulting chromium, molybdenum or tungsten promoted $VO(PO_3)_2$ compound (catalyst precursor) which has a surface area of approximately 5.0 to 15.0 $m^2/g$. requires a period of activation or conditioning for use in oxidizing the above indicated hydrocarbons. For the activation or conditioning the Group VIB metal-vanadium-phosphorus-oxygen catalyst precursor is subjected to temperatures which are at or above the hydrocarbon oxidation reaction temperatures which are from about 300° C. to 600° C. preferably from 450° C. to 550° C., under a flow of from about 0.2 volume percent to about 2.0 volume percent, preferably 0.5 to 1.5 volume percent in air of said hydrocarbon or mixture of hydrocarbons, to be oxidized and at an apparent contact time of from about 0.5 to 3.0 seconds, preferably 0.75 to 1.5 seconds for an appropriate period, to enable the hydrocarbon conversion to reach 90 percent or more, with subsequent temperature and flow rate adjustments to desired oxidation reaction conditions. Water vapor (steam) e.g., from about 10 to 35 mole percent may be added to the reactant hydrocarbon gases during the activation period and subsequent oxidation reaction. The length of time required for activation or conditioning of the catalyst precursor and to permit the catalyst performance to become stabilized depends on the temperature employed and contact time of the hydrocarbon-air mixture but generally will be from about 4 to 8 hours. Apparent contact time calculated in seconds is equal to the flow rate of the hydrocarbon-air feed mixture at cc/second, per cc of catalyst measured at ambient conditions. Once activated the Group VIB metal (chromium, molybdenum or tungsten) promoted $VO(PO_3)_2$ exhibits excellent performance as a catalyst for the oxidation of e.g., 1-butene, 2-butene, and 1,3-butadiene, or mixtures thereof, to maleic anhydride for extended periods of time.

The Group VIB metal promoted $VO(PO_3)_2$ catalyst of this invention may also be prepared in the presence of a suitable carrier such as silica gel, aluminosilicates, alumina, silicon carbide and carbon to provide a support for the catalyst and thus a surface which gives physical strength and stability to the catalyst material as well as a surface area which may be up to 50 $m^2/g$. on the support. The support is generally added in an amount of at least 10 percent by weight and preferably between about 50 to 60 percent by weight of the combined slurry mixture.

The following examples are provided to illustrate the invention in accordance with the principles of this invention but are not to be considered as limiting the invention in any way except as indicated by the appended claims.

In the Examples which follow that are directed to unsaturated hydrocarbon oxidation employing the instant chromium, molybdenum or tungsten promoted $VO(PO_3)_2$ catalyst, the reactions were run in a 5/8 inch inside diameter stainless steel U-tube reactor which was immersed in a fluidized sand bath for maintaining the temperature of reaction. The lower half of the U-tube reactor was filled with catalyst having an 8-16 mesh (Standard Sieve). The chromium, molybdenum or tungsten promoted $VO(PO_3)_2$ (precursor) catalyst was activated or conditioned in a stream of air with 1 volume percent of unsaturated hydrocarbon at a desired temperature for several hours at an appropriate apparent contact time over the catalyst. Following activation the temperature was decreased to the desired oxidation reaction temperature and the flow of hydrocarbon-air mixture, with or without the addition of steam, adjusted to the desired apparent contact time of between 0.5 to 3.0 seconds. The gaseous effluent oxidation reaction products from the reactor were passed through a series of water traps to adsorb the maleic anhydride and other by-products such as small amounts of acetic and acrylic acids; the maleic anhydride being converted to maleic acid in the aqueous solution. The gaseous effluent from the U-tube reactor was analyzed by InfraRed (I.R.) and gas chromatography to determine the concentration of carbon dioxide, carbon monoxide and any unconverted hydrocarbon. The aqueous solution containing the maleic acid was analyzed by gas chromatography to determine maleic anhydride yield and selectivity. Percent conversion of hydrocarbon and percent selectivity to maleic anhydride are calculated in mole percent.

EXAMPLE 1

A chromium promoted vanadium(IV)bis(metaphosphate) catalyst was prepared as follows: 75.2 grams (0.461 moles) of vanadyl sulfate ($VOSO_4$) along with 4.60 grams (0.046 moles) of chromic oxide ($CrO_3$) was added to 175 ml of acetic anhydride at ambient temperature of 25° C. with stirring. 85.0 grams (0.599 moles) of phosphorus pentoxide ($P_2O_5$) was slowly added to the solution with stirring forming a slurry and allowing the liberation of exothermic heat. Excess liquid was decanted from the slurry mixture and the resulting vanadyl sulfate-chromic oxide-phosphorus pentoxide product transferred to a furnace. The temperature of the furnace was increased at a rate of 1° C. per minute up to a maximum of 450° C. and maintained at that temperature for a period of 16 hours liberating the reaction gases. After cooling, the crystalline product was washed with water to remove any soluble residue. After drying at 120° C. the product was calcined in air at 500° C. for four hours to give a chromium promoted $VO(PO_3)_2$ catalyst (precursor) having an intrinsic surface area of approximately 6.6 $m^2/g$. After calcination the catalyst (precursor) was broken up (8-16 Standard Sieve mesh size) for use in the oxidation of 1-butene to maleic anhydride.

EXAMPLE 2

The procedure of Example 1 was repeated using 250 ml of acetic anhydride at 25° C. Excess liquid was decanted from the slurry which was heated in a furnace at a rate of 1° C. per minute to a maximum of 450° C. and maintained at that temperature for 15 hours liberating the reaction gases. The thermally reacted catalyst was water washed to remove soluble residue. After drying at 120° C. the product was calcined in air at a temperature of 525° C. for two hours to give a chromium promoted $VO(PO_3)_2$ catalyst (precursor) with an intrinsic surface area of approximately 12.9 $m^2/g$.

EXAMPLE 3

The procedure of example 1 was repeated employing 75.2 grams (0.461 moles) of vanadyl sulfate, 0.51 grams (0.005 moles) of chromic oxide and 250 ml of acetic anhydride to which was added 68.5 grams (0.482 moles) of phosphorus pentoxide at 26° C. Excess liquid was decanted and the slurry heated in a furnace at a rate of 1° C. per minute to a maximum of 450° C. and maintained at that temperature for a period of 12 hours liberating the reaction gases. After washing with water to remove soluble residue, drying at 120° C. and calcining in air at 500° C. for four hours a chromium promoted $VO(PO_3)_2$ catalyst (precursor) having an intrinsic surface area of 11.8 m$^2$/g. resulted.

EXAMPLE 4

An $SiO_2$-$Al_2O_3$ supported chromium promoted $VO(PO_3)_2$ catalyst was prepared as follows: 75.2 grams (0.461 moles) of vanadyl sulfate, 4.60 grams (0.046 moles) of chromic oxide along with 90.0 grams of $SiO_2$-$Al_2O_3$ was added to 250 ml of acetic anhydride with stirring. 85.0 grams (0.599 moles) of phosphorus pentoxide was slowly added to the solution with stirring forming a slurry and allowing the liberation of exothermic heat. Excess liquid was decanted from the slurry and the resulting mixture heated in a furnace at a rate of 1° C. per minute to a maximum of 450° C. and maintained for a period of 16 hours liberating the reaction gases. After cooling the reaction product was water washed to remove soluble residue and dried at 120° C. The dried product was calcined in air at 500° C. for 3 hours giving an $SiO_2$-$Al_2O_3$ supported crystalline chromium promoted vanadium(IV)bis(metaphosphate) catalyst (precursor) with an intrinsic surface area of 29.8 m$^2$/g.

EXAMPLE 5

A molybdenum promoted vanadium(IV)bis(metaphosphate) catalyst was prepared as follows: 75.2 grams of vanadyl sulfate along with 6.62 grams (0.046 moles) of molybdenum dioxide ($MoO_3$) was added to 175 ml of acetic anhydride at ambient temperature (26° C.) with stirring. 85.0 grams of phosphorus pentoxide was slowly added to the solution with stirring forming a slurry and allowing the liberation of exothermic heat. Excess liquid was decanted from the slurry mixture and the resulting vanadyl sulfate-molybdenum dioxide-phosphorus pentoxide product transferred to a furnace. The temperature of the furnace was increased at a rate of 1° C. per minute up to a maximum of 450° C. and maintained at that temperature for a period of 16 hours liberating the reaction gases. After cooling, the crystalline product was washed with water to remove soluble residue. After drying at 120° C. the product was calcined in air at 500° C. for four hours to give a molybdenum promoted $VO(PO_3)_2$ catalyst (precursor) having an intrinsic surface area of approximately 7.3 m$^2$/g. After calcination the catalyst (precursor) was broken up (8–16 Standard Sieve mesh size).

EXAMPLE 6

The procedure of Example 5 was repeated except that 250 ml of acetic anhydride was employed to prepare the slurry. After water washing, drying and calcination in air at 525° C. for four hours a molybdenum promoted $VO(PO_3)_2$ catalyst (precursor) having an intrinsic surface area of 13.8 m$^2$/g. resulted.

EXAMPLE 7

The procedure of Example 5 was repeated employing 75.2 grams (0.461 moles of vanadyl sulfate), 0.73 grams (0.005 moles) of molybdenum dioxide, 250 ml of acetic anhydride to which was added 68.5 grams (0.482 moles) of phosphorus pentoxide at 25° C. Excess liquid was decanted and the slurry heated in a furnace as in Example 5 for 16 hours liberating gases. After cooling, water washing, drying and calcination in air at 500° C. for four hours a molybdenum promoted $VO(PO_3)_2$ catalyst (precursor) having an intrinsic surface area of 14.8 m$^2$/g. resulted.

EXAMPLE 8

An $SiO_2$-$Al_2O_3$ supported molybdenum promoted $VO(PO_3)_2$ catalyst was prepared by forming a slurry of 75.2 grams vanadyl sulfate, 6.62 grams of molybdenum dioxide, 90.0 grams of $SiO_2$-$Al_2O_3$, 250 ml of acetic anhydride and 85.0 grams of phosphorus pentoxide with stirring and the liberation of heat. The slurry was introduced into a furnace and heated at a rate of 1° C. per minute to a maximum of 475° C. and maintained at that temperature for 12 hours liberating the reaction gases. After cooling the reaction product was water washed to remove soluble residue and dried at 120° C. The dried product was calcined in air at 500° C. for 3 hours giving an $SiO_2$-$Al_2O_3$ supported crystalline molybdenum promoted vanadium(IV)bis(metaphosphate) catalyst (precursor) with an intrinsic surface area of 29.4 m$^2$/g.

EXAMPLE 9

A tungsten promoted vanadium(IV)bis(metaphosphate) catalyst was prepared as follows: 75.2 grams of vanadyl sulfate along with 10.69 grams (0.461 moles) of tungstic oxide ($WO_3$) was added to 175 ml of acetic anhydride at ambient temperature (26° C.) with stirring. 85.0 grams of phosphorus pentoxide was slowly added to the solution with stirring forming a slurry and allowing the liberation of heat. Excess liquid was decanted from the slurry mixture and the resulting vanadyl sulfate-tungstic oxide-phosphorus pentoxide product transferred to a furnace. The temperature of the furnace was increased at a rate of 1° C. per minute to a maximum of 450° C. and maintained for a period of 16 hours liberating the reaction gases. After cooling the crystalline product was water washed to remove any soluble residue. After drying at 120° C. the product was calcined in air at 500° C. for two hours to give a tungsten promoted $VO(PO_3)_2$ catalyst (precursor) having an intrinsic surface area of approximately 6.5 m$^2$/g. After calcination the catalyst was broken up into an 8–16 Standard Sieve mesh size for use in the oxidation of hydrocarbons.

EXAMPLE 10

The procedure of Example 9 was repeated except that 250 ml of acetic anhydride was employed to prepare the vanadyl sulfate-tungstic oxide-phosphorus pentoxide slurry. After furnace preparation, cooling, water washing drying and calcination as in Example 9 a tungsten promoted $VO(PO_3)_2$ catalyst (precursor) having an intrinsic surface area of 11.8 m$^2$/g. resulted.

EXAMPLE 11

The procedure of Example 9 was repeated employing 75.2 grams of vanadyl sulfate, 1.19 grams of tungstic oxide, 250 ml of acetic anhydride to which was added 68.5 grams of phosphorus pentoxide at 26° C. Excess liquid was decanted and the slurry heated in a furnace as in Example 9 for 16 hours liberating the reaction gases. After cooling, water washing, drying and calcination as in Example 9 a tungsten promoted $VO(PO_3)_2$ catalyst (precursor) having an intrinsic surface area 10.6 m²/g. resulted.

EXAMPLE 12

A $SiO_2$-$Al_2O_3$ supported tungsten promoted VO(PO₃)₂ catalyst was prepared by forming a slurry of 75.2 grams vanadyl sulfate, 10.69 grams tungstic oxide, 90.0 grams $SiO_2$-$Al_2O_3$, 250 ml of acetic anhydride and 85.0 grams of phosphorus pentoxide with stirring and the liberation of exothermic heat. The slurry was heated in a furnace at a rate of 1° C. per minute to a maximum of 450° C. and maintained for 16 hours liberating the reaction gases. After cooling the product was water washed and dried at 120° C. The dried product was calcined in air at 500° C. for two hours giving an $SiO_2$-$Al_2O_3$ supported crystalline tungsten promoted vanadium(IV)-bis(metaphosphate) catalyst (precursor) with an intrinsic surface area of 21.5 m²/g.

EXAMPLE 13

A number of runs were made employing 30 ml. of the respective Cr, Mo and W promoted vanadium(IV)bis(metaphosphate) catalysts of Examples 2, 6 and 10 to oxidize 1-butene and 1,3-butadiene. The individual catalysts were loaded into the lower half of a U-tube reactor which was immersed in a fluidized sand bath. The Cr, Mo and W promoted catalysts (precursors) were activated in a stream of air, steam and 1 volume percent of the respective hydrocarbon at 490° C. for a period of 14 hours at an apparent contact time of approximately 3.0 seconds. Following activation of the catalyst the reaction temperature was decreased to the desired temperature and the apparent contact time adjusted to desired conditions. Results giving conversions and selectivities to maleic anhydride for the respective catalysts are shown in Table 1.

EXAMPLE 14

The procedure of Example 13 was repeated employing the $SiO_2$-$Al_2O_3$ supported chromium, molybdenum and tungsten promoted catalysts of Examples 4, 8 and 12 to oxidize 1-butene and 1,3-butadiene. The respective catalyst precursor was activated in a stream of air, steam and 1 volume percent of the respective hydrocarbon at 500° C. for 12 hours at an apparent contact time of 3.0 seconds. Following activation (conditioning) of the respective catalyst the reaction temperature was decreased to the desired temperature and the apparent contact time adjusted to the desired conditions. Results are shown in Table 2.

TABLE 2

| Run No. | Supported Catalyst Promoter | Hydrocarbon | Contact Time (sec.) | Temp. (°C.) | Mole % Steam | Mole %[1] Conversion | Mole %[2] Selectivity to Maleic Anhydride |
|---|---|---|---|---|---|---|---|
| 1 | $CrO_3$ | 1-butene | 0.85 | 365 | 20.5 | 98 | 64.1 |
| 2 | $CrO_3$ | 1,3-butadiene | 1.00 | 310 | 21.8 | 98 | 65.2 |
| 3 | $MoO_3$ | 1-butene | 1.00 | 425 | 21.4 | 97 | 64.5 |
| 4 | $MoO_3$ | 1,3-butadiene | 1.10 | 400 | 22.6 | 98 | 66.2 |
| 5 | $WO_3$ | 1-butene | 1.05 | 450 | 19.5 | 96 | 61.8 |
| 6 | $WO_3$ | 1,3-butadiene | 1.25 | 375 | 22.6 | 99 | 67.5 |

[1]% conversion determined by gas chromatography analyses of C₄ in effluent gas.
[2]% selectivity to maleic anhydride determined by gas chromatography.

We claim:

1. A method for the preparation of a promoted single phase crystalline vanadium(IV)bis(metaphosphate) hydrocarbon oxidation catalyst containing a Group VIB metal of the Periodic Table which comprises the steps of:
   forming a slurry of vanadyl sulfate, a Group VIB metal oxide selected from chromic oxide, molybdenum oxide or tungstic oxide, acetic anhydride and phosphorus pentoxide with the liberation of heat;
   introducing said slurry into a heating zone and maintaining said zone at a temperature of at least about 325° C. for a period sufficient for the liberation of gases and forming a Group VIB metal-vanadium-phosphorus reaction product;
   cooling the reaction product and washing with water to essentially remove any soluble residue;
   drying the water washed product and calcining in air to obtain a Group VIB metal containing single phase crystalline vanadium(IV)bis(metaphosphate) catalyst.

2. A method according to claim 1 wherein the molar ratio of Group VIB metal to vanadium, employed in the form of Group VIB metal oxide and vanadyl sulfate, is in the range of from about 1:10 to 1:150.

3. A method according to claim 2 wherein the ratio is 1:90.

4. A method according to claim 1 wherein the vanadyl sulfate-Group VIB metal oxide-acetic anhydride-

TABLE 1

| Run No. | Catalyst Promoter | Hydrocarbon | Contact Time (sec.) | Temp. (°C.) | Mole % Steam | Mole %[1] Conversion | Mole %[2] Selectivity to Maleic Anhydride |
|---|---|---|---|---|---|---|---|
| 1 | $CrO_3$ | 1-butene | 1.05 | 375 | 25.5 | 98 | 66.8 |
| 2 | $CrO_3$ | 1,3-butadiene | 1.25 | 350 | 30.8 | 99 | 65.2 |
| 3 | $MoO_3$ | 1-butene | 0.80 | 475 | 20.5 | 97 | 64.5 |
| 4 | $MoO_3$ | 1,3-butadiene | 1.25 | 425 | 22.5 | 98 | 65.0 |
| 5 | $WO_3$ | 1-butene | 1.00 | 460 | 26.5 | 99 | 66.3 |
| 6 | $WO_3$ | 1,3-butadiene | 1.10 | 400 | 29.8 | 99 | 67.4 |

[1]% conversion determined by gas chromatography analyses of C₄ in effluent gas.
[2]% selectivity to maleic anhydride determined by gas chromatography.

phosphorus pentoxide slurry is formed at ambient temperature.

5. A method according to claim 1 wherein at least stoichiometric quantities of vanadyl sulfate and phosphorus pentoxide are employed to form the slurry.

6. A method according to claim 1 wherein the amount of acetic anhydride employed is in the range of from about 1 to 4 moles per mole of the combined vanadyl sulfate, Group VIB metal oxide and phosphorus pentoxide employed.

7. A method according to claim 1 wherein the amount of acetic anhydride employed is from about 2 to 3 moles.

8. A method according to claim 1 wherein excess liquid is decanted from the slurry prior to introduction into the heating zone.

9. A method according to claim 1 wherein the slurry is reacted at a temperature of between about 400° C. and 460° C.

10. A method according to claim 1 wherein the Group VIB metal-vanadium-phosphorus reaction product is dried at a temperature of about 120° C. and calcined in air at a temperature of at least 450° C.

11. A method according to claim 1 wherein the Group VIB metal promoted single phase crystalline vanadium(IV)bis(metaphosphate) catalyst is prepared in the presence of a suitable carrier or support.

12. A method according to claim 11 wherein the carrier or support material is added to the Group VIB metal oxide, vanadyl sulfate, acetic anhydride, phosphorus pentoxide slurry.

13. A method according to claim 12 wherein the carrier or support is an aluminosilicate.

14. A method according to claim 1 wherein the Group VIB metal containing single phase crystalline vanadium(IV)bis(metaphosphate) catalyst in the unsupported state has an intrinsic surface area of from about 5 to 15 $m^2/g$.

15. A method according to claim 1 wherein the Group VIB metal oxide is chromic oxide.

16. A method according to claim 1 wherein the Group VIB metal oxide is molybdenum oxide.

17. A method according to claim 1 wherein the Group VIB metal oxide is tungstic oxide.

* * * * *